Figure 3:
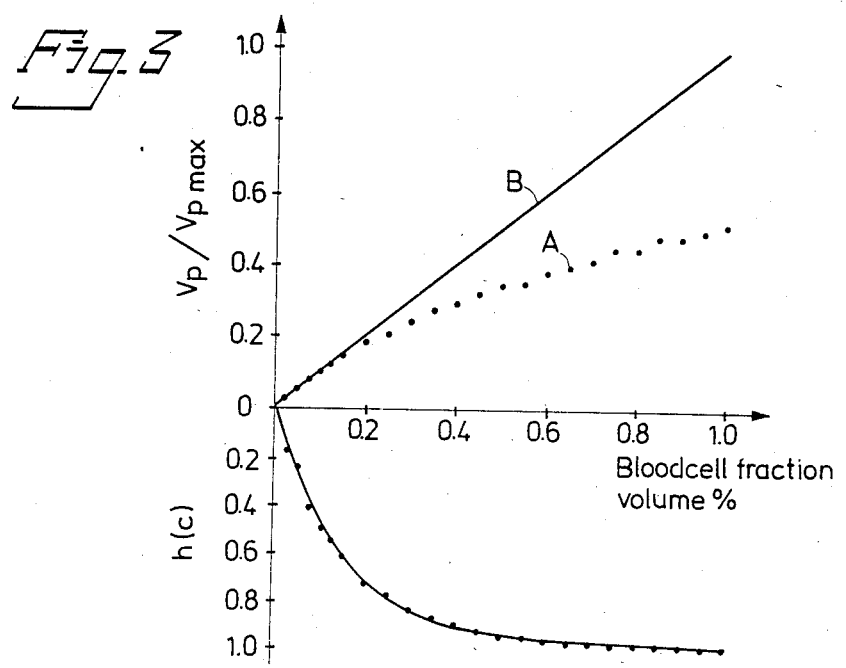
Figure 4:
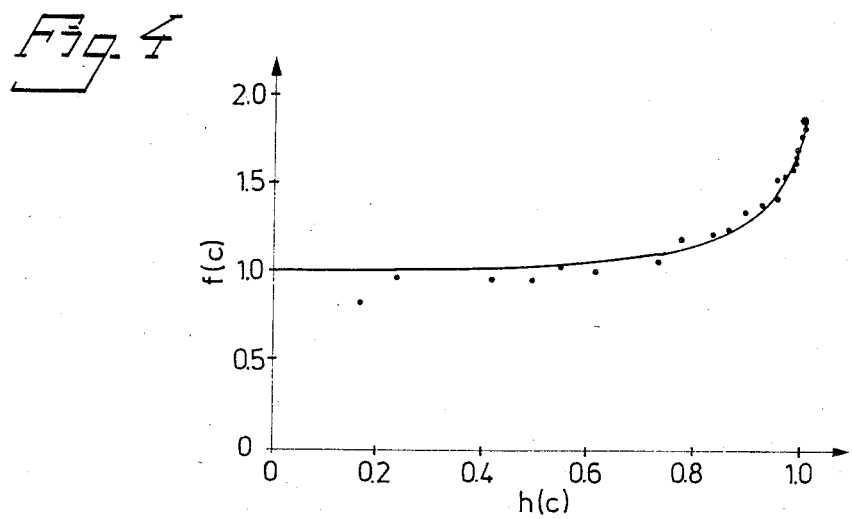
Figure 5:
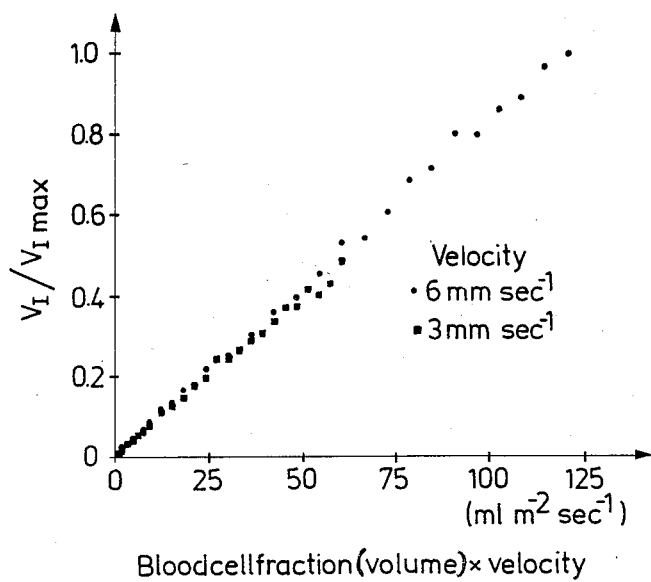
Figure 6:
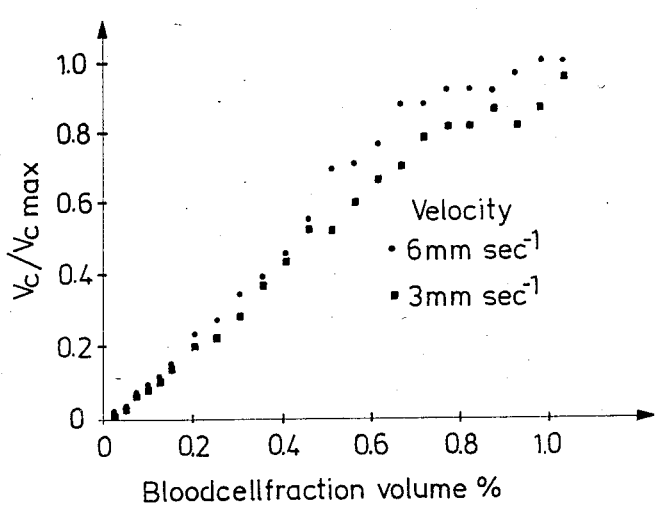

United States Patent [19]

Nilsson

[11] Patent Number: 4,590,948
[45] Date of Patent: May 27, 1986

[54] METHOD AND APPARATUS FOR MEASURING THE BLOOD FLOW IN THE SUPERFICIAL BLOOD VESSELS OF TISSUE

[75] Inventor: Gert Nilsson, Lund, Sweden

[73] Assignee: Perimed KB, Stockholm, Sweden

[21] Appl. No.: 689,489

[22] Filed: Jan. 7, 1985

[30] Foreign Application Priority Data

Jan. 20, 1984 [SE] Sweden ................................ 8400289

[51] Int. Cl.$^4$ .............................................. A61B 5/02
[52] U.S. Cl. ..................................... 128/666; 128/691
[58] Field of Search ............... 128/633, 634, 665, 666, 128/691

[56] References Cited

U.S. PATENT DOCUMENTS 4,109,647  8/1978  Stern et al. .
4,476,875 10/1984  Nilsson et al. ...................... 128/666

OTHER PUBLICATIONS

Dennis Watkins & G. Allen Holloway, Jr., "An Instrument to Measure Cutaneous Blood Flow Using the Doppler Shift of Laser Light", IEEE Transactions on Biomedical Engineering, vol. BME-25, No. 1, Jan. 1978, pp. 28-33.

M. D. Stern, "In Vivo Evaluation of Microcirculation by Coherent Light Scattering", Nature, vol. 254, Mar. 6, 1975.

Michael D. Stern & Donald L. Lappe, "Measurement of Local Tissue Blood Flow by Laser Doppler Spectroscopy", Federation Proceedings, vol. 35, No. 3, Mar. 1, 1976.

Gert Nilsson, Torsten Tenland & P. Ake Oberg, "A New Instrument for Continuous Measurement of Tissue Blood Flow by Light Beating Spectroscopy", IEEE Transactions on Biomedical Engineering, vol. BME-27, No. 1, Jan. 1980, pp. 12-19.

Gert Nilsson, Torsten Tenland & P. Ake Oberg, "Evaluation of a Laser Doppler Flowmeter for Measurement of Tissue Blood Flow", IEEE Transactions on Biomedical Engineering, vol. BME-27, No. 10, Oct. 1980, pp. 597-604.

Primary Examiner—Kyle L. Howell
Assistant Examiner—John C. Hanley
Attorney, Agent, or Firm—Lahive & Cockfield

[57] ABSTRACT

In a method and an apparatus for measuring the superficial blood flow in tissue, a section of the tissue is irradiated with monochromatic light from a laser source. Light scattered by moving blood cells and adjacent stationary structure within a part of the irradiated section is collected and passed to a photo-detector arrangement, which produces an output signal containing fluctuating signal components, a Doppler signal, deriving from interference between light components having differing frequencies due to having been scattered by moving blood cells and thereby subject to frequency shifts. The Doppler signal contains information concerning the number of blood cells present and the velocity at which they move. By means of a signal processor, there is derived from the Doppler signal a signal which is linearly related to the blood flow expressed as the product of the number of blood cells and their average velocity of movement, and a signal which is linearly related to the number of blood cells present.

13 Claims, 8 Drawing Figures

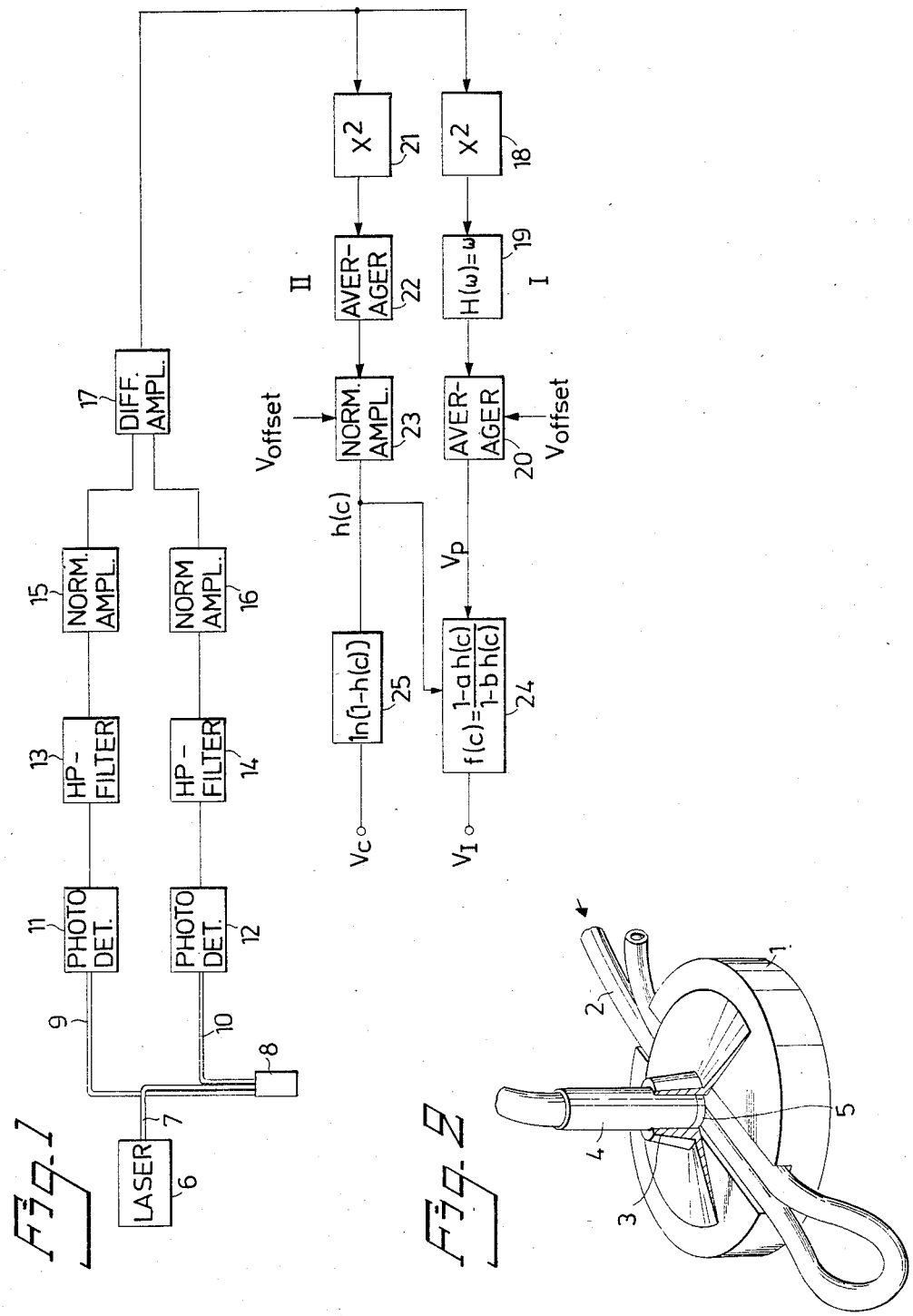

METHOD AND APPARATUS FOR MEASURING THE BLOOD FLOW IN THE SUPERFICIAL BLOOD VESSELS OF TISSUE

The present invention relates to a method and a corresponding apparatus for determining the microvascular blood flow in tissue.

The invention is based on a known technique in which a section of the tissue surface is irradiated with monochromatic light from a laser-light source through optical fibres, and the light scattered by the moving blood cells and adjacent stationary structures within a part of the irradiated section is collected and transmitted to a photodetector through further optical fibres. The photo-detector produces an output signal which, in addition to a d.c. voltage component, also includes fluctuating signal components deriving from interference at the surface of the photo-detector of light components whose frequency has been shifted by scattering against moving blood cells, a Doppler shift, partly mutually and partly with light components which have solely been scattered by the stationary structures and the frequency of which has thus not been shifted. The fluctuating signal components of the photodetector output signal, hereinafter referred to as the Doppler signal for the sake of simplicity, thus contains information concerning both the number of blood cells present within that section of the tissue from which the scattered light passed to the photo-detector originates, and the velocity at which said cells move.

This known technique for measuring the blood flow in tissue is found described, inter alia, in IEEE Trans. Biomed. Engineering, Vol. BME-25, No. 1, January 1978, "An Instrument for Measuring Cutaneous Blood Flow Using the Doppler Shift or Laser Light", D. Watkins and G. A. Hollowway; Nature Vol. 254, March 1975, "In Vivo Evaluation of Microcirculat by Coherent Light Scattering", N. D. Stern; Fed. Proc. Vol. 35, No. 3, 1976, "Measurement of Local Tissue Blood Flow by Laser Doppler Spectroscopy", N. D. Stern and D. L. Lappe; IEEE Trans. Biomed. Engineer, Vol. BME-27, No. 1, January 1980, "A New Instrument for Con Measurement of Tissue Blood Flow by Light Beating Spectroscopy", Gert. E. Nilsson, Torsten Tenland, P. Åke Öberg; and IEEE Trans. Biomed. Engineering, VOL. BME-27, No. 10, October 1980, "Evaluations of a Laser Doppler Flowmeter for Measurement of Tissue Blood Flow", Gert E. Nilsson, Torsten Tenland and P. Åke Öberg; and also in the U.S. Pat. No. No. 4,109,647 and the Swedish Patent Specification No. 419,678. An instrument designated Periflux and obtainable from Perimed, Stocknolm, Sweden, with which this technique can be carried out, is also available on the market.

According to the aforementioned known technique there is either used a single photo-detector, to which light backscattered from a part of the illuminated tissue area is passed, or two photo-detectors to which backscattered light is passed from two adjacent portions of the illuminated area, the output signals from these two photodetectors being subtracted one from the other. In both cases there is obtained a resultant photo-detector signal, which contains the aforementioned Doppler signal with information of the number of blood cells present and the velocity at which they move. Certain types of disturbances stemming from the laser source are greatly reduced, however, when using two photo-detectors which receive backscattered light from separate parts of the tissue and the output signals of which are subtracted one from the other, as suggested by Nilsson et al and as used in the Periflux-instrument, this reduction being highly advantageous and affording a practical utility when taking measurements of tissue blood flow.

Irrespective of whether one or two photo-detectors are used, when practicing the described method, difficulty is experienced in deriving from the Doppler signal produced by the photo-detector arrangement a signal which represents a correct measurement of the blood flow, expressed as the product of the number of blood cells, or their concentration in the blood, and the average velocity of said blood cells. There is namely a relatively complicated relationship between, on one hand, the magnitude and frequency distribution of the Doppler signal and, on the other hand, the number of blood cells present and the velocity at which they move. Thus, the Doppler signal contains firstly signal components deriving from homodyne interference, i.e. mutual interference, between light components with varying frequency shifts, and secondly signal components deriving from heterodyne interference, i.e. interference between Doppler shifted light components and unshifted light components scattered in static structures. Moreover, part of the Doppler shifted light components may have been scattered successively in two or more moving blood cells and therewith undergone multiple Doppler shifts.

In the forementioned article by Nilsson et al in IEEE Trans. Biomed. Engineer., Vol. BME-27, No. 10, October 1980, it is proposed to derive from the Doppler signal produced by the photo-detector arrangement, i.e. from the differential signal between the output signals of the two photo-detectors and subsequent to removing the d.c. voltage signal component, a signal which is proportional to the mean value of the expression $$\int_{\omega_1}^{\omega_2} \omega P(\omega) d\omega \qquad (1)$$

where $\omega$ is the frequency of the Doppler signal, $P(\omega)$ is its power density as a function of its frequency, i.e. the unnormalized spectral power distribution of the Doppler signal, and $\omega_1$ and $\omega_2$ are the limit frequencies of a frequency band containing at least the major part of the Doppler signal.

It can be shown theoretically that this expression is related linearly with the blood flow expressed as the product of the number of moving blood cells and their average velocity, provided that the signal components in the Doppler signal caused by homodyne interference can be ignored and that the number of multiple frequency shifts is also negligibly small, i.e. provided that the number of blood cells is small. On the other hand, however, when there is a large number of blood cells in the tissue, the probability of photons being scattered successively in more than one moving blood cell, resulting in multiple frequency shifts, can no longer be discounted, and neither can that part of the Doppler signal caused by homodyne interference. The linear relationship between the aforementioned expression and the true blood flow then ceases to apply, such that the expression provides a lower value than the true blood flow. Consequently, when the aforegiven expression is used as the output signal of the instrument, and a high value is obtained for the measured blood flow, it is not known whether this high flow value has been generated by a limited number of blood cells moving at a high velocity, in which case the measuring value obtained is correct, or by a large number of blood cells moving at a low average velocity, in which case the measuring value obtained is too low. In practice, this latter problem occurs primarily when measuring tissue rich in blood, for example in delated finger tips, lips and mucous membranes.

The object of the present invention is to provide, in respect of a method and corresponding apparatus of the aforementioned kind for measuring tissue blood flow, an improved method and a correspondingly improved apparatus for processing the Doppler signal obtained from the photodetector arrangement, so that there is obtained an output signal which is linearly related to the blood flow, expressed as the product of the number of blood cells and their average velocity, even for high concentrations of blood cells.

The characterizing features of the method and apparatus according to the invention are set forth in the accompanying claims.

Figure 7:
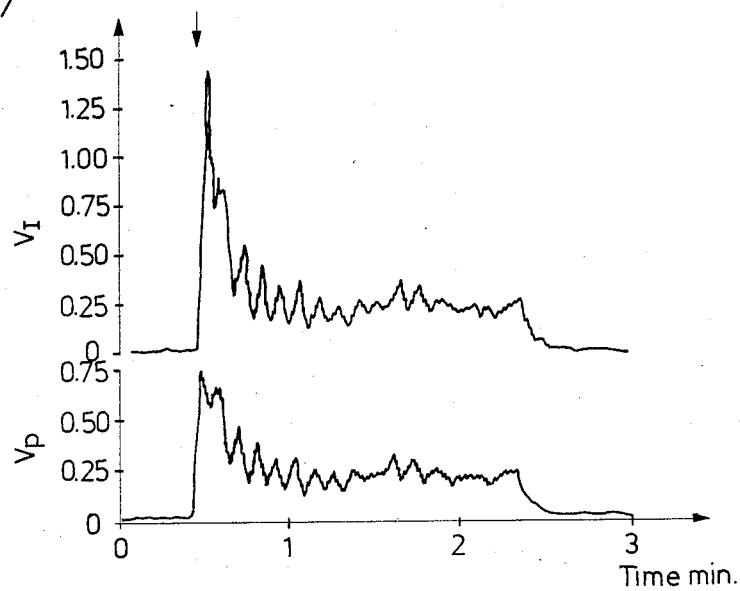
Figure 8:
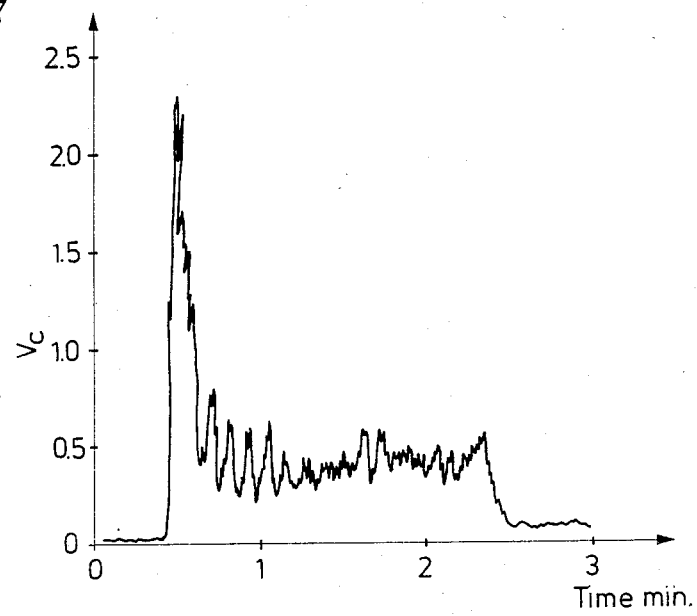

The invention will now be described in more detail with reference to the accompanying drawings, in which FIG. 1 is a simplified block diagram of an apparatus for measuring tissue blood flow, said apparatus including a signal processor designed in accordance with the invention;

FIG. 2 is a schematic perspective view of a mechanical model, which was used in developing the invention for studying the relationship between various signals in the measuring device and a blood flow of well defined values with regard to the concentration and average velocity of the blood cells;

FIGS. 3, 4, 5 and 6 are diagrams illustrating the relationship between various signals in a measuring device according to the invention and the blood cell concentration and the blood flow respectively, these diagrams being used to explain the invention; and FIGS. 7 and 8 are diagrams illustrating the shape of the measuring signal in the case of practical, comparison tests carried out with a measuring device according to the invention and with the previously known Periflux instrument.

For the purpose of investigating the relationship between the aforementioned expression (1), proposed by Nilsson et al in IEEE Trans. Biomed. Engineering, Vol. BME-27, No. 10, October 1980, as a measurement of the blood flow, and actual blood flow expressed as the product of the number of blood cells and their average velocity, there was used the previously mentioned Periflux instrument from Perimed, Stockholm, Sweden, which provides an output signal proportional to said expression, and a mechanical model constructed in the manner schematically illustrated in FIG. 2, said model being designed to optically resemble tissue through which blood flows. In this model, the static tissue structure is simulated by means of a semi-transparent plate 1 made of polyacetal resin. This plate scatters the incident light beam diffusely, and has a scattering cross section which is similar to that of healthy Caucasian skin. Fixedly arranged in a slot in the upper side of the plate is a double-folded polyethylene tube 2, having connected to one end thereof a precision pump, which is not shown in the drawing. Mounted on the plate 1 symmetrically above the polyethylene tube is a holder 3 for accommodating the measuring probe of the Periflux instrument. FIG. 2 shows the measuring probe 4 of the instrument inserted in the holder 3. A thin film 5 of polyacetal resin is inserted in the bottom of the holder 3 to ensure that the incident light is scattered diffusely prior to said light striking the blood cells flowing through the polyethylene tube 2. With respect to the design and functioning mode of the Periflux-instrument used, the reader is referred to the aforementioned article in IEEE Trans. Biomed. Engineering, Vol. BME-27, No. 10, October 1980. This instrument gave an output signal, hereinafter designated $V_p$, proportional to the mean time value of the expression $$\int_{\omega_1}^{\omega_2} \omega P(\omega)d\omega - V_{offset} \quad (2)$$

in which $V_{offset}$ is an offset signal for compensating the photo-detector noise which, together with the Doppler signal, forms part of the fluctuating signal components from the photo-detector arrangement, said offset signal being calculated from the total photo-detector current. In the experiments, the values $\omega_1$ and $\omega_2$ were set to 20Hz and 12kHz respectively.

The experiments were carried out on human blood obtained from a blood bank, said blood being heparinized, diluted with physiological saline and carefully agitated prior to being used.

Experiments made with a constant, relatively high bloodcell concentration of 1% (volume) and a varying average blood-cell velocity showed a substantially linear relationship between the output signal $V_p$ from the instrument, representing the magnitude of the blood flow, and the average velocity of the blood cells up to a velocity of 8 mm/s. No such linear relationship was obtained, however, between the output signal $V_p$ and the blood-cell concentration with a constant average blood-cell velocity. The output signal $V_p$ was registered for two average velocities of the blood cells, namely 3 and 6 mm/s, and for various blood-cell concentrations from 0 to 1% (volume). The result of these measurements is plotted in the upper part of the diagram shown in FIG. 3, in the form of the measuring points which describe a curved line A. It shall be noticed that the ordinate of the diagram is normalized to the maximum output signal $V_{Pmax}$ for the measurement in question. It is obvious from this that the output signal $V_p$ of the instrument will not constitute a correct measurement of the magnitude of blood flow at higher blood-cell concentrations. The output signal should rightly follow the full-line curve B. It is also obvious that the non-linear relationship between the output signal $V_p$ and the actual blood flow, expressed as the product of the blood-cell concentration and the average velocity of said cells, is solely dependent upon the concentration of the blood cells.

The present invention is based on the concept of correcting the output signal $V_p$ of the known instrument, so that said signal becomes linearly dependent on the blood flow, independently of the blood-cell concentration, i.e. so that the curved line A for the output signal $V_p$ is made to conform to the desired rectalinear curve B. It will be realised that this correction of the output signal $V_p$ of the known instrument must be made in dependence on the prevailing concentration of blood cells, which has a value not known in advance.

Theoretical considerations show that the blood-cell concentration can be stated by the expression $$c = -k_1 \ln(1-h(c)) \quad (3)$$

in which c is the blood-cell concentration expressed in the volume percentage of moving blood cells, $k_1$ is an instrument constant, and h(c) is defined by the expression $$h(c) = \frac{k_2}{i_T^2} \int_{\omega_3}^{\omega_4} P(\omega)d\omega \quad (4)$$

in which $k_2$ is an instrument constant, $i_T$ is the total photo-detector current, and $\omega_3$ and $\omega_4$ are the limit frequencies for a frequency band within which at least the major part of the Doppler signal from the photo-detector arrangement lies.

It will be seen from expressions (3) and (4) that the quantity h(c) is unambiguously solely dependent upon the blood-cell concentration and approaches the value 1 (one) for high blood-cell concentrations. It will also be seen from the expression that (4) the quantity h(c) can be readily obtained in instrument, since $P(\omega)$ is the power density of the Doppler signal as a function of its frequency. Thus, a signal representing the quantity h(c) can be readily obtained, by squaring and averaging the Doppler signal from the photo-detector arrangement.

A signal proportional to the quantity h(c) was derived in this way from the Doppler signal of the photo-detector arrangement, when carrying out the aforedescribed experiment. The values for h(c) thus obtained are plotted in the lower part of the diagram shown in FIG. 3, as a function of the blood-cell concentration, the value for h(c) being normalized to 1 for high blood-cell concentrations.

There was also calculated an empirical correction factor f(c), by which the output signal $V_P$ of the instrument should be multiplied in order to provide the linear relationship according to curve B between the output signal and the blood flow. Obviously, this correction factor can be seen as a function of the quantity h(c), which is singularly dependent upon the blood-cell concentration and linearly proportional to the total power of the Doppler signal. The thus calculated values for the empirical correction factor f(c) have been plotted in the diagram shown in FIG. 4 as a function of h(c). A curve which fits this empirically calculated correction factor can be represented by the expression $$f(c) = (1 - a \cdot h(c))/1 - b \cdot h(c)) \quad (5)$$

where a and b are empirical constants, which in the present case have the values a=0.885 and b=0.939 respectively. Other functions of h(c) are also conceivable, however. Thus, a signal which is proportional to the said correction factor f(c) can be derived from the signal proportional to h(c), with the use of non-linear electric circuits, and utilized as an amplifying factor for the signal $V_P$, so that, in accordance with the invention, a measuring signal $V_I$ is obtained from the instrument according to the expression $$V_I = f(c) V_P \quad (6)$$

It is apparent that such an output signal $V_I$ from the measuring arrangement will exhibit the desired linear relationship with the blood flow, expressed as the product of the blood-cell concentration and the average velocity of the blood cells, even at higher blood-cell concentrations.

It will be evident from the aforementioned expression (3) that a signal which is linearly proportional to the blood-cell concentration can also be obtained, by applying the signal representing the magnitude h(c) to a logarithmic amplifier, which produces an output signal $V_c$ corresponding to the expression $$V_c \sim \ln(1-h(c)) \quad (7)$$

It will be understood from the aforegoing that a measuring apparatus according to the invention may, for example, be designed in the manner schematically illustrated in FIG. 1. This measuring apparatus comprises, in a manner known from the previously cited article by Nilsson et al, in IEEE Trans. Biomed. Engineering, Vol. BME-27, No. 10, October 1980, a laser source 6, whose light is passe, via optical fibre 7, to the measuring probe 8 of the apparatus, said probe being intended to be brought close to the surface of the tissue in which the superficial blood flow is to be measured. Light scattered from parts of the irradiated tissue is passed through optical fibres 9 and 10, to two photo-detectors 11 and 12. The output signals from photo-detectors are passed through high-pass filters 13 and 14 respectively, for the removal of the d.c. voltage component in the photo-detector current, and from there to normalizing amplifiers 15 and 16 respectively, in which the signals are normalized in relation to the total photodetector current. The normalized signals from the amplifiers 15 and 16 are applied to a differential amplifier 17, the output signal of which corresponds to the difference between the two input signals. Thus, this output signal is the previously mentioned Doppler signal, containing information concerning the number of moving blood cells in the irradiated section of the tissue, and the velocity at which said cells move.

The Doppler signal is applied, in a known manner, to a first array of signal processing circuits, generally referenced I, where the signal is squared in a circuit 18, and then passed through a filter circuit 19 having the transfer function $H(\omega) = \omega$, and is finally passed to a averaging circuit 20. Thus, the output signal obtained with this circuit is the previously mentioned signal $V_p$.

In accordance with the invention, the Doppler signal obtained from the differential amplifier 17 is also passed to a second array of signal processing circuits, generally referenced II. In this, the Doppler signal is squared in a circuit 21, whereafter the signal is passed to a averaging circuit 22, and then through a normalizing amplifier 23, in which the signal is normalized, so as to obtain the value 1 (one) for high blood-cell concentrations. Thus, the output signal from the circuit 23 is the previously mentioned signal h(c). The normalizing amplifier 23 can be set by immersing the measuring probe 8 into a stable emulsion containing a large number of light scattering particles.

The signal h(c) from circuits II is applied as a control signal to a non-linear amplifying circuit 24, to the input of which the signal $V_P$ from circuits I is applied and which has an amplifying factor f(c) in accordance with the previously mentioned expression (5). Thus the signal $V_P$ is amplified by said amplifying f f(c), so as to obtain the previously mentioned signal $V_I$ on the output of circuit 24. This signal is the desired measuring signal, which is linearly proportional to the blood flow expressed as the product of blood-cell concentration and the velocity at which said blood cells move.

The apparatus also includes a logarithmic amplifying circuit 25, to which the signal h(c) is applied and which has the amplifying factor ln(1−h(c)) and the output signal of which is the previously mentioned signal $V_c$, which is linearly proportional to the blood-cell concentration.

In view of the fact that the Doppler signal from the differential amplifier 17 also contains the noise signal of the photo-detectors, an advantage is gained by subtracting in both the circuits I and the circuits II an offset signal $V_{offset}$ from the signal $V_P$ and the signal h(c) respectively, so as to compensate for the photodetector noise. This offset signal can be calculated from the photo-detector current, as described by Nilsson et al.

A measuring apparatus constructed in the aforedescribed manner in accordance with the invention was tested, with the aid of the previously described model illustrated in FIG. 2. The results obtained are shown in the diagram in FIG. 5, which shows the value of the signal $V_I$ as a function of the actual blood flow expressed as the product of blood-cell concentration and the average velocity of the blood cell, and in the diagram in FIG. 6, which illustrates the signal $V_c$ as a function of the actual blood-cell concentration. The measurements were taken at two mutually different, constant velocities, namely 3 mm/s and 6 mm/s respectively, and for varying blood-cell concentrations between 0 and 1% (volume). As will be seen from the Figures, tne signal $V_I$ and the signal $V_c$ both scale substantially linearly.

Tests comparing the invention with the previously known technique were also carried out, by registering the signal $V_P$ in accordance with the previously known technique and registering the signal $V_I$ in accordance with the invention, when measuring the flow of blood in palmar skin during reactive hyperemia, produced by rapid deflation of a pressure cuff placed around the upper arm. The shape of the respective signals $V_P$ and $V_I$ is illustrated in the diagram in FIG. 7. As can be seen, the signal $V_P$ obtained with the known technique markedly underestimated the blood flow immediately after the release of the cuff. The high blood-flow value produced immediately after the release of the cuff is due to dilatation of the microrelease vasculature and a resulting, initially high but temporary increase in the blood-cell concentration, this also being confirmed by the diagram in FIG. 8, which illustrates the shape of the signal $V_c$. The signal $V_P$ obtained with the known technique greatly underestimates the high blood-flow value, because said signal is not capable of taking into account the effect of multiple scattering in the large number of blood cells, and of homodyne interference at the photodetector surface.

Although the invention has been described with reference to a measuring apparatus provided with two photo-detectors in accordance with Nilsson et al, it will be understood that the invention can also be practiced with a measuring apparatus having only one photo-detector. As will be understood, other modifications of the measuring apparatus are also possible within the scope of the invention.

I claim:

1. A method for determining the blood flow in the superficial blood vessels of tissue, comprising the steps of irradiating a section of the surface of said tissue with monochromatic light;

capturing light scattered by moving blood cells and adjacent stationary structures within a part of the irradiated tissue section;

passing said captured, scattered light to a photodetector arrangement for producing an electric output signal containing fluctuating signal components, hereinafter referred to as the Doppler signal, which derive from interference between light components received by the photo-detector arrangement and having mutually different frequencies due to having been scattered by moving blood cells and thereby subject to shift in their frequency, said Doppler signal containing information concerning the number of blood cells present and the velocity at which they move;

deriving from said Doppler signal produced by said photo-detector arrangement a first signal which represents the mean time value of the expression $$\int_{\omega_1}^{\omega_2} \omega P(\omega)\, d\omega$$

where $\omega$ is the frequency of the Doppler signal, $P(\omega)$ is the power density of the Doppler signal as a function of its frequency, and $\omega_1$ and $\omega_2$ represent limit frequencies of a frequency band within which at least a major part of the Doppler signal is located;

deriving from said Doppler signal a second signal which is solely dependent on the number of blood cells present, but not their velocity of movement;

amplifying said first signal with an amplifying factor which is dependent on said second signal; and using said amplified signal as a measurement of the magnitude of the blood flow.

2. A method as claimed in claim 1, wherein said second signal is substantially proportional to the mean time value of the expression $$\int_{\omega_3}^{\omega_4} P(\omega)\, d\omega$$

where $\omega_3$ and $\omega_4$ are limit frequencies of a frequency band within which at least a substantial part of the Doppler signal is located.

3. A method as claimed in claim 2, wherein said amplifying factor corresponds to the expression 1−a h(c))/(1−b h(c))

where a and b are empirically determined constants and h(c) is the value of said second signal dependent solely on the number of blood cells and normalized to a value 1 for high blood-cell concentrations, and in which the constants a and b are so selected that said amplified signal exhibits a substantially linear relationship with the blood flow, expressed as the product of the number of blood cells and their average velocity of movement.

4. A method as claimed in claim 1, wherein said first signal is obtained by squaring the Doppler signal, passing the squared signal through a filter having the transfer function $H(\omega)=\omega$ and then averaging the signal.

5. A method as claimed in claim 1, wherein said second signal is obtained by squaring the Doppler signal and averaging the squared signal.

6. A method as claimed in claim 1, comprising the additional step of subtracting from both said first signal and said second signal a signal which is dependent on the total output signal of the photo-detector arrangement, in order to compensate for noise generated in the photodetector arrangement.

7. A method as claimed in claim 2, comprising the additional step of deriving from said second signal a third signal which is-proportional to the expression $$\ln(1-h(c))$$

where h(c) is said signal dependent solely upon the number of blood cells present, and using said third signal as a measurement of blood-cell concentration.

8. An apparatus for determining the blood flow in the superficial blood vessels of tissue, comprising
   a monochromatic light source;
   means for irradiating a section of the tissue surface with light from said light source;
   means for collecting light scattered by moving blood cells and adjacent stationary structures within a part of said irradiated section;
   a photo-detector arrangement for receiving said collected, scattered light and producing a corresponding electric output signal; and
   a signal processor including high-pass filter circuits to which the output signal of said photo-detector arrangement is applied for removing d.c. signal components therefrom,
   first circuit means receiving the output signal of said high-pass filter circuits for producing a first signal representing the mean time value of the expression $$\int_{\omega_1}^{\omega_2} \omega P(\omega)\, d\omega$$

where $\omega$ is the frequency of said output signal, $P(\omega)$ is the power of said output signal as a function of its frequency, and $\omega_1$ and $\omega_2$ are limit frequencies of a frequency band within which at least a major part of said output signal lies,
   second circuit means receiving the output signal of said high-pass filter circuits for producing a second signal proportional to the mean time value of the expression $$\int_{\omega_3}^{\omega_4} \omega P(\omega)\, d\omega$$

where $\omega_3$ and $\omega_4$ are limit frequencies of a frequency band within which at least a major part of said output signal lies, and
   a controllable amplifying circuit having a signal input to which said first signal is applied, a control input to which said second signal is applied, and an amplifying factor controlled by and dependent on said second signal,
   the output signal of said amplifying circuit constituting a measurement of the blood flow.

9. An apparatus as claimed in claim 8, wherein the amplifying factor of said amplifying circuit is proportional to the expression $$(1-a\,h(c))/(1-b\,h(c))$$

where (h(c)) is said second signal and a and b are empirically determined constants of such values that the output signal of the amplifying circuit is a substantially linear measurement of the blood flow, expressed as the product of the number of blood cells present and their average velocity of movement.

10. An apparatus as claimed in claim 8, wherein said first circuit means include a filter circuit having the transfer function $H(\omega)=\omega$, a squaring circuit, and an averaging circuit.

11. An apparatus as claimed in claim 8, wherein said second circuit means include a squaring circuit and an averaging circuit.

12. An apparatus as claimed in claim 8, wherein said first and said second circuit means include means for subtracting from said first and said second signals a signal component dependent on the total output signal of the photo-detector arrangement, in order to compensate for noise generated in the photo-detector arrangement.

13. An apparatus as claimed in claim 8, wherein said signal processor includes third circuit means receiving said second signal for producing an output signal proportional to the expression $$\ln(1-h(c))$$

where h(c) is said second signal, said output signal from said third circuit means constituting a measurement of the blood-cell concentration.

* * * * *